United States Patent [19]

Bucalo

[11] 4,172,446
[45] * Oct. 30, 1979

[54] APPARATUS FOR COLLECTING BODY FLUIDS

[76] Inventor: Louis Bucalo, 155 Roberts St., Holbrook, N.Y. 11741

[*] Notice: The portion of the term of this patent subsequent to Dec. 21, 1993, has been disclaimed.

[21] Appl. No.: 645,380

[22] Filed: Dec. 30, 1975

Related U.S. Application Data

[63] Continuation-in-part of Ser. No. 534,893, Dec. 20, 1974, Pat. No. 3,998,211.

[51] Int. Cl.$^2$ ............................................. A61B 10/00
[52] U.S. Cl. ................................... 128/769; 128/270; 435/294
[58] Field of Search ............. 128/2 W, 2 F, 2 R, 1 R, 128/260, 275; 195/103.5 R, 139, 140

[56] References Cited

U.S. PATENT DOCUMENTS

| | | | |
|---|---|---|---|
| 3,057,344 | 10/1962 | Abella et al. | 128/2 F |
| 3,118,439 | 1/1964 | Perrenoud | 128/2 F |
| 3,315,660 | 4/1967 | Abella | 128/2 F |
| 3,485,235 | 12/1969 | Felson | 128/2 F |
| 3,688,763 | 9/1972 | Cromarty | 128/2 F X |
| 3,844,285 | 10/1974 | Laby | 128/260 |
| 3,845,770 | 11/1974 | Theeuwes | 128/260 |
| 3,853,116 | 12/1974 | Bucalo | 128/1 R |
| 3,926,521 | 12/1975 | Ginzel | 128/2 F X |

Primary Examiner—Kyle L. Howell
Attorney, Agent, or Firm—Steinberg & Blake

[57] ABSTRACT

Apparatus for collecting body fluids at an internal cavity of the body of a living being. An enclosure is introduced into a body cavity with the enclosure in a contracted or evacuated condition. The enclosure has structure permitting body fluid to enter into the enclosure but not to flow out of the latter. A suitable triggering structure is provided to respond to the presence of a body fluid in order to trigger the release of the enclosure for collection, whereupon the enclosure sucks body fluid into the interior of the enclosure, with the enclosure having a structure such as a one-way valve which provides conditions permitting the fluid to flow into the enclosure but not to flow out of the latter. Thereafter, the enclosure is removed from the body cavity so that information can be obtained with respect to the fluid which is collected in the enclosure. The enclosure preferably contains an additive for providing a predetermined desired result with respect to a collected body fluid.

18 Claims, 6 Drawing Figures

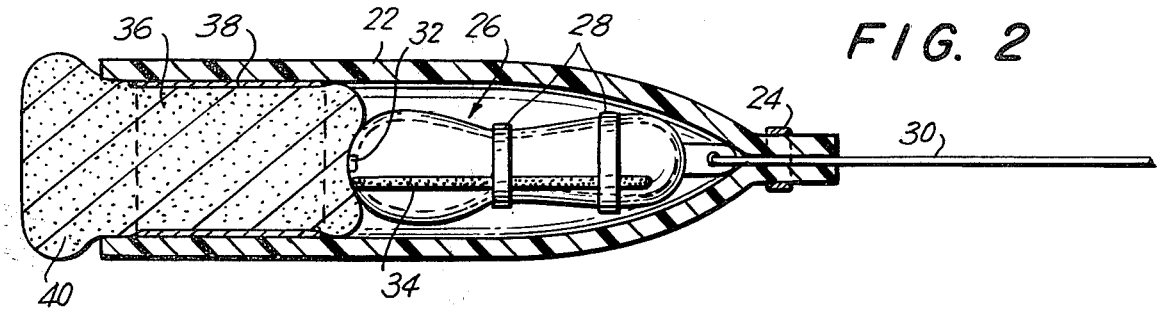
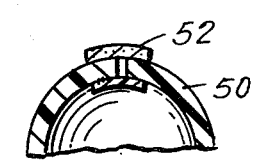
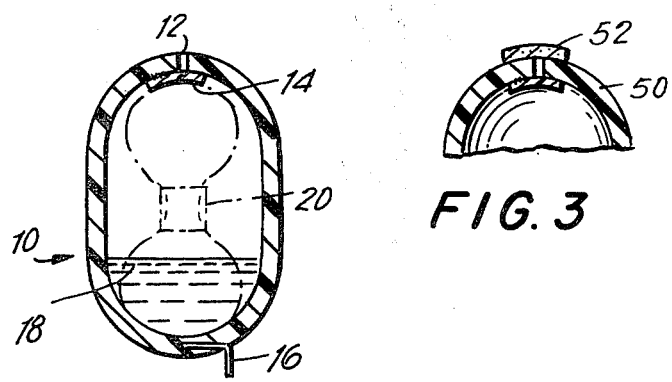
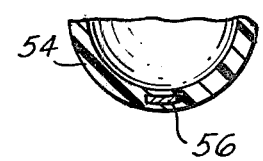
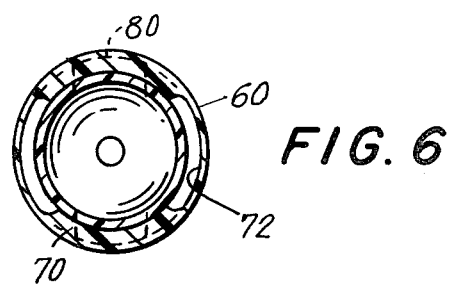

APPARATUS FOR COLLECTING BODY FLUIDS

CROSS REFERENCE TO RELATED APPLICATION

This application is a continuation-in-part of copending application Ser. No. 534,893, filed Dec. 20, 1974, now U.S. Pat. No. 3,998,211.

BACKGROUND OF THE INVENTION

The present application relates to devices for collecting body fluids.

As is well known, specimens of certain body fluids of living beings are required in order to be used for culturing purposes so as to determine the presence or absence of certain microorganisms or for analysis of the body specimens themselves.

While it is conventional to utilize a swab in order to take a specimen from the interior of the body of a living being, and then apply the specimen to a suitable culturing medium, these conventional procedures involve a number of drawbacks because of the unavoidable influence on the microorganisms during transfer thereof from the body to the culturing medium at the exterior of the body as well as due to the fact that the culturing conditions do not precisely match the conditions in the body so that it is possible for microorganisms to grow in the body but not in the culturing medium. Current methods of collecting specimens are often painful and embarrassing to the patient.

SUMMARY OF THE INVENTION

It is accordingly a primary object of the present invention to provide a structure which will avoid the above drawbacks.

In particular, it is an object of the present invention to provide a structure according to which it is possible to collect a body fluid in an enclosure which remains in the body cavity where the body fluid is collected, so that collection by way of a swab or invasive techniques are not required.

Moreover, it is an object of the present invention to provide an apparatus according to which reliable collection of a desired specimen is assured. In other words with the present invention it is possible to avoid procedures with a false specimen, as is possible with previously known procedures such as a specimen which has been altered by stomach acids, enzymes, and the like.

Furthermore, it is an object of the present invention to provide a structure of this type which will not have any undesirable influence on the body from which the specimen is taken.

Also, it is an object of the present invention to provide a structure of the above type which is simple and inexpensive while at the same time being highly reliable.

According to the invention there is introduced into a body cavity a location where there is a body fluid which is suspected to have certain microorganisms therein, an enclosure which is evacuated or made of an elastic material and initially contracted. This enclosure has an opening through which a body fluid can enter the enclosure, while a structure such as a one-way valve is provided to prevent the body fluid which enters the enclosure from travelling out of the latter. A suitable triggering mechanism is provided for causing the enclosure which initially is in a contracted condition to expand in the body cavity so as to suck body fluid into the enclosure. The enclosure can be permitted to remain in the body cavity for a certain period of time which will encourage growth of suspected microorganisms in the fluid which is collected in the enclosure. For this purpose no particular nutrient medium or the like may be required inasmuch as the microorganism can grow very often in the presence of the body fluid with which the microorganism is transferred into the enclosure. However, it is also possible to situate, according to a further feature of the invention, a suitable additive in the enclosure so as to promote achievement of a desired result with respect to the specimen, such as a pH control, gas environment, selective antibiotic, or enzyme neutralizer. Additionally, specimens which can be collected by swallowing the device may have incorporated a magnetic member to aid in separation of the capsule from the feces.

BRIEF DESCRIPTION OF DRAWINGS

The invention is illustrated by way of example in the accompanying drawings which form part of this application and in which:

FIG. 1 is a schematic sectional elevation of one possible embodiment of a device according to the invention, for carrying out the method of the invention;

FIG. 2 is a longitudinal sectional elevation of a further embodiment of a device according to the invention for carrying out the method of the invention;

FIG. 3 fragmentarily illustrates in a schematic manner a further embodiment of a capsule according to the invention;

FIG. 4 is a fragmentary schematic illustration of yet a further feature of the invention;

FIG. 5 is a longitudinal sectional elevation of another embodiment of the invention; and FIG. 6 is a transverse section of the structure of FIG. 5 taken along line 6—6 of FIG. 5 in the direction of the arrows.

DESCRIPTION OF PREFERRED EMBODIMENTS

Referring to FIG. 1, there is illustrated therein a flexible container 10 made of a suitable elastic sheet material such as, for example, polyethylene. This container 10 is formed at one end with a small opening 12. Situated next to the opening 12 in the container 10 is a one-way valve means 14 which may be in the form of a springy flap fastened as by suitable adhesive to the inner surface of the enclosure 10 adjacent but to one side of the opening 12. Alternatively, a ball check valve may be used or the enclosure may be evacuated and sealed with a soluble seal. As will be apparent from the description which follows, with this latter type of enclosure, the capsule may be substantially rigid and evacuated. Thus, the container 10 forms an enclosure means which has at a wall part thereof a transfer means formed by way of the opening 12 and the one-way valve means 14 to create conditions according to which fluid can flow through and beyond this wall part of the enclosure means into the interior of the enclosure means through the opening 12 but cannot flow out of the enclosure means. The enclosure means 10 may initially take the form of a pair of shell halves which are fused together in order to form the complete flexible springy enclosure means, and before the halves are joined to each other the one-way valve means 14 may be situated in the interior of the enclosure means in the manner illustrated in FIG. 1. Also, when one of the enclosure halves is molded, it can be molded in part around an end of a string 16 which is fragmentarily illustrated, although the string 16 can also be fastened to the enclosure means in other ways such as by suitable adhesive. This string 16 facilitates removal of the enclosure from the body, for example.

Although it is not essential, there is illustrated in FIG. 1 an additive 18 situated in the interior of the enclosure means. This additive is provided in order to promote a predetermined result with respect to the fluid, tissues carried with the fluid, or microorganisms which may be present in the fluid. Thus, the additive 18 may take the form of a suitable nutrient medium, catalytic additive, or a suitable preservative. Thus, if the blood is the collected body fluid, then the preservative medium may take the form of a suitable citric acid or in the case of certain microorganisms, the additive 18 may take the form of suitable broths which are known to promote the growth of certain microorganisms.

However, it is to be emphasized that the terms "nutrient" and "preservative" do not necessarily signify positive feeding or nourishing and positive preserving. Thus, a nutrient may also be considered a medium which will prevent the growth of undesired microorganisms while permitting the growth of those microorganisms about which certain information is desired. In the same way, a preservative may be a preservative in the sense that it kills those microorganisms which might have a deleterious effect on the microorganisms or specimens about which the information is desired. The preservative may prevent stomach enzymes from destroying tissues.

Moreover, it is to be emphasized that it is perfectly possible for the desired microorganisms in many cases to grow in the body fluid in which microorganisms are suspended and with which the microorganisms are collected in the enclosure means 10. Thus it is not essential to use any additive since the body fluid itself may serve as a suitable growth medium in some cases.

In order to use the structure of FIG. 1 according to the method of the invention, this structure is introduced into a body cavity in a contracted condition as illustrated in phantom lines in FIG. 1. In order to maintain the enclosure means in the contracted condition, it is surrounded at an intermediate portion by a trigger means formed by a band 20 made of a material which will dissolve or otherwise disappear because of conditions prevailing in the body cavity. Thus in response to the temperature prevailing in a body cavity the material of the band 20 may disintegrate or by contact with liquid in the body cavity the band 20 may dissolve. In any event, upon disintegrating or dissolving the band 20 releases the enclosure means 10 from the contracted or compressed condition thereof shown in phantom lines in FIG. 1, so that the enclosure means 10 expands in order to suck body fluid into the interior of the enclosure means through the opening 12, the one-way valve means 14 preventing return of collected body fluid out of the enclosure means back into the body so that a suitable shielding effect is achieved. The enclosure means may be permitted to remain in the body cavity for a length of time sufficient for suspected microorganisms to grow either in the body fluid itself or in connection with a suitable additive 18 as set forth above, and after passage of a certain length of time the enclosure means may be removed from the body cavity with the string 16 being used for this purpose is necessary. It is to be emphasized that the enclosure means of the invention may be introduced into any body cavity such as the vagina so that the opening 12 is situated next to the cervix, or the enclosure means of the invention may be introduced into the anus in order to collect specimens at the latter region of the body. In addition, it is possible to provide an arrangement according to which a patient will swallow the enclosure means so that it will pass through the digestive tract with the band 20 being designed to dissolve at a certain point by the action of natural stomach acids or preconsumed actuating chemicals along the digestive tract in order to collect a specimen which can be examined after the enclosure means passes out of the body of the patient.

Referring now to FIG. 2, the embodiment of the invention which is illustrated therein includes an outer elongated non-absorbent or slowly absorbent sleeve 22 which in the illustrated example is flexible. This sleeve may be made of a suitable plastic such as polyethylene. The sleeve 22 is open at its left end while it is closed at its right end as by being surrounded by a suitable band 24. However, before being surrounded by the band 24, there is situated in the non-absorbent sleeve 22 an enclosure means 26 having substantially the same construction as the enclosure means 10 of FIG. 1. This enclosure means 26 can be made of the same material and it is initially situated in the sleeve 22 in a compressed or contracted condition as illustrated. At one end of the enclosure means 26, the latter has an integral tab connected to one end of a pull string 30 which extends through the right end of the sleeve 22 before the latter is gathered together by the band 24. Thus when the band 24 closes the right end of the sleeve 22, the pull string 30 extends through and beyond the sleeve 22 while being connected by way of the tab to the enclosure means 26.

This enclosure means 26 in the illustrated example is surrounded by a trigger means formed by a pair of compressing or contracting bands 28 which are of the same nature as the band 20 in that these bands 28 will dissolve when engaged by a body liquid so as to release the enclosure means 26 for expansion. This enclosure means 26 is provided at its left end as viewed in FIG. 2, with a transfer means formed by a small opening 32, corresponding to the opening 12, and also with a one-way valve means situated adjacent the small opening 32.

In addition, in the embodiment of FIG. 2, a wick 34 is situated at the exterior of the enclosure means 26. This wick 34 is preferably surrounded by the bands 28 which thus serve to hold the wick 34 in engagement with the exterior surface of the enclosure means 26. The wick means may be at the exterior of the band or the wick function may be performed by an absorbable sleeve 22 which absorbs the fluid at a relatively slow rate, as pointed out below, with a suitable absorbent medium being situated between such a sleeve and the bands in the space between the enclosure means 26 and the sleeve 22.

The end of the enclosure means 26 where the opening 32 and one-way valve means are located is in engagement with an absorbent matrix 36 in the form of a suitable sponge material such as a suitable foam plastic or in the form of cotton wadding or the like. Thus it will be seen that this absorbent matrix 36 bears directly against the opening 32 and one-way valve associated therewith. Also it will be seen that the wick 34 directly engages the absorbent matrix 36 being compressed between the latter and the left end of the enclosure means 26. In the illustrated example where the sleeve 22 is flexible and compressible, the absorbent matrix 36 passes through a substantially rigid interior sleeve 38 situated within and surrounded by the sleeve 22, so that this sleeve 38 prevents compacting of the matrix 36 by the muscles of the body.

The matrix 36 extends out beyond the left open end of the non-absorbent sleeve 22 in the manner shown in FIG. 2. Thus, beyond the open end of the sleeve 22, the absorbent matrix 36 has an enlarged bulging portion 40, the remainder of the absorbent means 36 being somewhat more compressed within the rigid sleeve 38.

As was pointed out above, it is possible to provide a sleeve 22 which is absorbent but to a lesser degree than the matrix 36. Such a sleeve may directly engage the bands or an absorbent medium in the form of suitable wadding may fill the space between the trigger bands 28 and the enclosure 22. With such an embodiment by making the sleeve 22 of a material which absorbs liquid at a relatively slow rate, there is an assurance that the fluid will flow through the matrix 36 and be in engagement with the end of the enclosure means 26 where the valve means is located by the time that the fluid can pass through the sleeve 22 of lesser absorbency and through any medium between this sleeve and the bands for dissolving the latter. In this way also it is possible to assure a proper sequence of operations according to which the triggered release of the enclosure means for expansion must take place after the fluid has been absorbed through the matrix into engagement with the end of the capsule where the valve means is located. However, it is to be emphasized that the specific disclosure described above and shown in FIG. 2 is preferred inasmuch as with a non-absorbent sleeve and with the wick extending from the matrix to the trigger bands as illustrated, a far more reliable structure is provided.

As a result of the construction shown in FIG. 2, it is only possible for body fluid to reach the enclosure means 26 after traveling through the absorbent medium 36 after first engaging the end 40 thereof. When the body fluid is sucked, as by capillary action into the absorbent means 36, this body fluid will engage the wick 34 and will by capillary action flow along the wick 34 into engagement with the bands 28 so as to dissolve the latter thus triggering the expansion of the enclosure means 26. It will be noted that as a result of this feature it is not possible for the body fluid to dissolve the trigger bands before the enclosure means is in a condition for supplying body fluid into the interior of the enclosure means. In other words it is possible to visualize a situation where before an opening such as the opening 12 of FIG. 1 or the opening 32 of FIG. 2 is situated at the proper location, the body fluid dissolves the triggering band so that the enclosure expands without collecting the desired fluid. This undesirable result is avoided with the construction of FIG. 2. Thus according to FIG. 2 only when the body fluid flows through the absorbent means 36 into engagement with the opening 32 and the wick 34 will the body fluid travel further along the wick 34 in order to release the triggering bands 28 so that a highly reliable collection of body fluid is achieved in this way.

Furthermore, it is to be noted that because the outer portion 40 of the absorbing means 36 bulges in the manner illustrated, this outer portion 40 will frictionally scrape specimens from the wall of a body passage such as a vagina, for example, thus achieving in this way a reliable specimen of body fluid which will be absorbed by the means 36 and then collected in the enclosure means 26.

The interior of the enclosure means 26 may have an additive as described above or may simply be left without an additive inasmuch as suspected microorganisms may grow in the body fluid itself as pointed out above. After the device has remained in the body for a required length of time, the pull string 30 may be used to remove the device of FIG. 2 from the body, and then upon removal of the enclosure means 26 from the interior of the sleeve 22, it is possible to determine whether or not certain microorganisms are present.

Of course, in the event that the sleeve 22 itself is of sufficient rigidity, it is not necessary to use the internal substantially rigid sleeve 38.

In the embodiment of FIG. 1, the enclosure means is made of an elastic material so that it can be compressed to assume the phantom line position of FIG. 1 with or without evacuation of the interior of the enclosure means. With the embodiment of FIG. 3, the enclosure means 50 is made of a substantially rigid plastic material which will not collapse, but in this case the interior of the enclosure is evacuated so as to be at less than atmospheric pressure, and it will be noted that this construction also has a one-way valve means. The opening with which the one-way valve means cooperates is to form a transfer means at a wall part of the enclosure means in the embodiment of FIG. 3 covered by a trigger means formed by a body of material 52 capable of responding to conditions in the body for automatically becoming released from the opening which initially is covered and sealed by the body 52. Thus after evacuating the interior of the substantially rigid enclosure 50, the opening through which the enclosure 50 communicates with the outer atmosphere is sealed by way of the body 52. This body 52 is made of a material which can, for example, dissolve when engaging liquid in the body or which responds to the temperature conditions in the body for disintegrating and uncovering the opening so that when this opening is uncovered liquid in the body can then be sucked in through the one-way valve which prevents the liquid from escaping, this sucking in of the liquid being brought about because of the evacuated atmosphere provided in the interior of the substantially rigid enclosure 50.

FIG. 4 illustrates an embodiment where the enclosure means 54 may take the form of an enclosure as shown in FIG. 1 or as shown in FIG. 3. With this embodiment there is embedded in the wall of the enclosure a magnetic body 56. Thus this body 56 need not be a permanent magnet but it is made of a material which will respond to magnetism. Thus in this case where the enclosure means 54 is swallowed and passes through the digestive system, it will as pointed out above receive in its interior a desired body fluid at a certain point along the digestive tract. This enclosure means 54 will discharge from the body with feces, and in order conveniently to remove the body 54 from the feces, it is only necessary to situate a permanent magnet adjacent the body 54 so that the magnetic body 56 will respond to facilitate separation of the enclosure means 54 from the feces.

A further embodiment of the invention is illustrated in FIGS. 5 and 6. Thus in this embodiment there is also an exterior non-absorbent sleeve 60 which may be made of the same material as the sleeve 22 of FIG. 2. However, in this case the sleeve 60 has at its right end an inwardly extending lip 62 which is received in a peripheral groove formed at one end of an end cap 64 which can be snapped onto the end of the sleeve 60 with the lip 62 received in the groove of the cap 64. This cap 64 can simply be twisted off from the sleeve 60 in order to be separated therefrom, as indicated in phantom lines in FIG. 5. Thus, the end cap 64 may be made of a somewhat flexible plastic material. At one end it has a pull string 66 connected thereto as illustrated.

In the interior of the sleeve 60 of non-absorbent material, this sleeve is formed with annular groove 68 which has at its right side, as viewed in FIG. 5, an internal flange 70 which is interrupted so as to have gaps 72 as illustrated in FIG. 6. In this way this construction provides a bayonet type of connection.

The enclosure means 74 is made of an elastic material similar to the enclosure means of FIG. 2. This enclosure means is surrounded by the constricting trigger bands 76 which yield when receiving fluid from the wick 78 in the same way as described above in connection with FIG. 2. The enclosure means 74, however, has at its left end, in addition to the one-way valve means and opening communicating through the valve means with the interior of the enclosure means a pair of opposed lugs 80 which are capable of passing through the gaps 72 and into the groove 68 whereupon the enclosure means can be turned so as to situate the lugs 80 in the groove 68 in line with the flange 70 beyond the gap 72 thereof, so that in this way a bayonet connection is made for the enclosure means in the sleeve 60.

The sleeve 60 carries in its interior an absorbent matrix 82 which may be identical with the matrix 36 described above, and if desired in the sleeve 60 there may be a substantially rigid sleeve surrounding the part of the matrix 82 which is in the interior of the sleeve so as to prevent collapse thereof by the muscles of the body as described above. The right end of the matrix 82, as viewed in FIG. 5, directly engages the left end of the enclosure means 74, and the wick 78 extends from the matrix 82 to the trigger bands 76 for transmitting the liquid thereto so that when the bands yield the enclosure means 74 will expand to the phantom line position shown in FIG. 5. Thus, this embodiment will also provide the same results as the embodiment of FIG. 2, but is superior thereto in certain respects such as the capability of twisting off the rear cap 64 so as to give access to the enclosure means which can then be removed simply by turning the enclosure means so that the lugs 80 will pass out through the gaps 72 of the bayonet connection.

Of course, the outer sleeve can be made itself of a substantially rigid material so that an inner rigid sleeve is not required.

What is claimed is:

1. For use in connection with collecting fluids from a cavity of a body of a human being or animal, enclosure means having a shape and size for occupying a position in a body cavity with one wall part of said enclosure means situated adjacent a location where the body fluid which is to be collected is situated and with said enclosure means defining a hollow interior closed off from the outer atmosphere at least to an extent sufficient to prevent escape of fluid from the interior to the exterior of said enclosure means, transfer means situated at said one wall part of said enclosure means for automatically transferring a fluid forming a body specimen through and beyond said wall part of said enclosure means from the exterior to the interior of said enclosure means in a manner which is not controlled from the exterior of the body, while the enclosure means is in the body, and trigger means operatively connected with said enclosure means for automatically initiating operation of said transfer means after said enclosure means is situated in a body cavity.

2. The combination of claim 1 and wherein an additive is situated in said enclosure means for favoring a desired result with respect to a collected body specimen.

3. The combination of claim 1 and wherein said enclosure means is made of elastic material, said trigger means which is operatively connected with said enclosure means maintaining the latter in a contracted condition when introduced into the body cavity, said trigger means being capable of responding to conditions in the body cavity for releasing the enclosure means for expansion in the body cavity, and said transfer means including a passage at said one wall part of said enclosure means through which a body specimen is sucked into said enclosure means upon expansion thereof.

4. The combination of claim 3 and wherein a one-way valve means is carried by said enclosure means at said opening thereof for permitting body fluid to enter through said opening while preventing body fluid from escaping out of said enclosure means through said opening thereof.

5. The combination of claim 1 and wherein a magnetic body is carried by said enclosure means in a wall portion thereof so that the enclosure means will respond to magnetic attraction to be removed from a medium in which the enclosure means may be situated.

6. The combination of claim 4 and wherein said trigger means includes at least one band surrounding said enclosure means and maintaining the latter in a compressed condition, said trigger means responding to contact with a body fluid to yield and release said enclosure means for expansion.

7. The combination of claim 6 and wherein an outer sleeve means which is made of a material which will absorb body fluid at a relatively slow rate houses said enclosure means together with said trigger means and band, an absorbent means carried by said sleeve means in the interior thereof in engagement with said opening of said enclosure means, said absorbent means having a much faster rate of absorption than said sleeve means and having a free end portion extending outwardly beyond said sleeve for directly engaging a body fluid at an end region of said sleeve, whereby the body fluid must travel through said absorbent means into engagement with the opening of said enclosure means.

8. The combination of claim 6 and wherein an outer sleeve means made of material which will not absorb body fluid houses said enclosure means together with said trigger means and band, a wick engaging said trigger means at the exterior of said enclosure means for conveying to said trigger means a body fluid for causing said trigger means to yield so that the latter will release said enclosure means for expansion, and absorbent means carried by said sleeve means in the interior thereof in engagement with said wick and said opening of said enclosure means, said absorbent means having a free end portion extending outwardly beyond said sleeve for directly engaging a body fluid at an end region of said sleeve, whereby the body fluid must travel through said absorbent means into engagement with the opening of said enclosure means and said wick.

9. The combination of claim 8 and wherein said outer sleeve means is substantially rigid.

10. The combination of claim 8 and wherein said outer sleeve means has an end cap which is removable from the remainder of said outer sleeve means to give access to said enclosure means, and bayonet-connection means for connecting said enclosure means to said sleeve means releasably in the interior of said sleeve means.

11. The combination of claim 8 and wherein said absorbent means is in the form of a sponge.

12. The combination of claim 8 and wherein said sleeve is made of a flexible material, and an internal rigid sleeve surrounding said absorbent means with in said flexible sleeve to prevent compacting of said absorbent means in the interior of said flexible sleeve.

13. The combination of claim 12 and wherein an additive is situated in said enclosure means for favoring a desired result with respect to a collected body specimen.

14. The combination of claim 8 and wherein a string is fixed to and extends from said sleeve for facilitating retraction thereof from a body cavity.

15. The combination of claim 8 and wherein said absorbent means at its end which projects beyond said sleeve bulges outwardly beyond the latter so as to be capable of performing a scraping function when moving along the wall of a body cavity.

16. The combination of claim 1 and wherein said enclosure means has an evacuated interior, said trigger means which is operatively connected with said enclosure means maintaining the latter in its evacuated condition when introduced into the body cavity, said trigger means being capable of responding to conditions in the body cavity for placing the interior of said enclosure means in a condition for receiving a body specimen, and said transfer means including a passage at said one part of said enclosure means through which a body specimen may be received in said enclosure means.

17. The combination of claim 16 and wherein said enclosure means is made of a substantially rigid material and has an opening forming said passage, and said trigger means being in the form of a body of material sealing said opening but capable of responding to conditions in the body cavity for releasing said opening to provide communication between the evacuated interior of said enclosure means and the exterior thereof, so that a body specimen will then be sucked into said enclosure means.

18. The combination of claim 1 and wherein said enclosure means is made of elastic material, an outer sleeve means made of a material which will not absorb body fluid housing said enclosure means and absorbent means carried by said sleeve means in the interior thereof in engagement with said transfer means and having a free end portion extending outwardly beyond said sleeve for directly engaging a body fluid at an end region of said sleeve, whereby body fluid will travel through said absorbent means into engagement with said transfer means, said sleeve means including a means for rendering the interior thereof accessible for removal of said enclosure means from said sleeve means so that after said enclosure means has initially been contracted and expands to suck a body fluid in from said absorbent means, the enclosure means with the body fluid therein can be removed from said sleeve means.

* * * * *